(12) United States Patent
Nagoya

(10) Patent No.: US 7,622,312 B2
(45) Date of Patent: Nov. 24, 2009

(54) METHOD FOR EVALUATING DOPANT CONTAMINATION OF SEMICONDUCTOR WAFER

(75) Inventor: Takatoshi Nagoya, Gunma (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 311 days.

(21) Appl. No.: 11/886,059

(22) PCT Filed: Feb. 6, 2006

(86) PCT No.: PCT/JP2006/301962
§ 371 (c)(1),
(2), (4) Date: Sep. 11, 2007

(87) PCT Pub. No.: WO2006/103832
PCT Pub. Date: Oct. 5, 2006

(65) Prior Publication Data
US 2008/0108155 A1    May 8, 2008

(30) Foreign Application Priority Data
Mar. 25, 2005  (JP) ............................ 2005-089246

(51) Int. Cl.
*H01L 21/66* (2006.01)
(52) U.S. Cl. .................. 438/17; 257/E21.531; 324/765
(58) Field of Classification Search .......... 257/E21.531; 324/765; 438/17
See application file for complete search history.

(56) References Cited

U.S. PATENT DOCUMENTS

| | | | | |
|---|---|---|---|---|
| 6,140,131 A | * | 10/2000 | Sunakawa et al. | 436/72 |
| 6,303,396 B1 | * | 10/2001 | Ring et al. | 438/14 |
| 6,462,538 B2 | * | 10/2002 | Harada | 324/224 |
| 6,489,776 B1 | * | 12/2002 | Stowe et al. | 324/458 |
| 6,878,038 B2 | * | 4/2005 | Swedek et al. | 451/6 |
| 6,884,634 B2 | * | 4/2005 | Suzuki et al. | 438/4 |
| 6,914,442 B2 | * | 7/2005 | Ebara | 324/750 |
| 7,030,633 B1 | * | 4/2006 | Qiu et al. | 324/754 |

(Continued)

FOREIGN PATENT DOCUMENTS

JP    A 01-012277    1/1989

(Continued)

OTHER PUBLICATIONS

ASTM Designation: F 723-82; (1982); Standard Practice for Conversion Between Resistivity and Dopant Density For Boron Doped and Phosphorus-Doped Silicon; pp. 1267-1283.

*Primary Examiner*—Asok K Sarkar
(74) *Attorney, Agent, or Firm*—Oliff & Berridge, PLC

(57) ABSTRACT

The present invention provides a method for evaluating dopant contamination of a semiconductor wafer, wherein a resistivity of a bulk portion of the semiconductor wafer is measured by an eddy current method, a resistivity in a surface layer of the semiconductor wafer is measured by a surface photovoltage method, and an amount of dopant contamination of the semiconductor wafer is calculated from a difference between a value of the resistivity of the bulk portion measured by the eddy current method and a value of the resistivity in the surface layer measured by the surface photovoltage method. As a result of this, it is possible to provide the method for evaluating dopant contamination of a semiconductor wafer, which can measure the amount of dopant contamination of a whole surface layer of the semiconductor wafer without contact, nondestructively, and accurately.

24 Claims, 6 Drawing Sheets

U.S. PATENT DOCUMENTS

| | | | |
|---|---|---|---|
| 7,078,919 B2 * | 7/2006 | Prussin | 324/719 |
| 7,106,425 B1 * | 9/2006 | Bultman et al. | 356/73 |
| 7,141,992 B2 * | 11/2006 | Ohno et al. | 324/750 |
| 2002/0090746 A1 * | 7/2002 | Xu et al. | 438/17 |

FOREIGN PATENT DOCUMENTS

| | | |
|---|---|---|
| JP | A 2004-055935 | 2/2004 |
| JP | A 2004-207601 | 7/2004 |

\* cited by examiner (a)

(b)

METHOD FOR EVALUATING DOPANT CONTAMINATION OF SEMICONDUCTOR WAFER

TECHNICAL FIELD

The present invention relates to a method for evaluating contamination due to a dopant of a semiconductor wafer.

BACKGROUND ART

In recent years, LSIs (Large Scale Integrated Circuit) have been progressing to be higher integrated and semiconductor devices have been progressing to be finer increasingly, and in line with them, it is required to improve controllability of a carrier concentration in a semiconductor wafer, for example, a silicon wafer for semiconductor device manufacturing as much as possible. Particularly, since a carrier concentration near the surface of the silicon wafer affects characteristics of the semiconductor device, such as resistivity, it is required to measure a concentration of an additional impurity (dopant) contained near the surface thereof with high precision and high sensitivity.

Note that a dopant described here is an intentionally added impurity in order to control a carrier concentration in a semiconductor wafer to control a resistivity thereof.

Generally, in order to control a carrier concentration in a silicon wafer, boron (B) is mainly used when a conductivity type is a p-type, and phosphorus (P) is mainly used when it is an n-type, as the dopant. Makers of semiconductor wafers control an additional amount of the dopant upon growing silicon single crystals to be used as materials of the silicon wafers, or the like so that the silicon wafers to be manufactured may have desired carrier concentrations or resistance values, and manufacture the silicon wafers.

Meanwhile, makers of semiconductor devices set a standard, for example, the resistivity is 8 to 12 Ω·cm, and have semiconductor wafers which satisfy the standard included in boxes and delivered. As a result, respective resistivities of the semiconductor wafers within the delivered box are different within the standard (within the range of 8 to 12 Ω·cm). The makers of the semiconductor devices put such silicon wafers that have respectively different resistivities within standard into semiconductor device manufacturing processes, and manufacture the semiconductor devices.

Meanwhile, there has occurred a problem, so-called dopant contamination, in which a dopant is unintentionally mixed from surrounding environments or the like without intentionally adding it for resistivity adjustment while manufacturing of a semiconductor device. Particularly, since an original dopant concentration is very low when a silicon wafer with the extremely high resistivity is used, the carrier concentration is changed only by a small amount of dopant being mixed in the silicon wafer, so that the resistivity thereof may be changed significantly.

For example, in a heat treatment process for manufacturing a semiconductor device, an unnecessary contaminant dopant, such as boron, phosphorus, or the like mixes in the semiconductor wafer from an atmosphere within a heat treat furnace, the heat treat furnace, or the like and the semiconductor wafer is contaminated, so that the carrier concentration may be changed. Such a dopant contamination causes a drop of a manufacturing yield of the semiconductor devices, and deterioration in quality thereof. Therefore, it is particularly important to evaluate and manage the dopant contamination in the manufacturing process of the semiconductor wafer and the manufacturing process of the semiconductor device.

As the method for evaluating dopant contamination described above, there is a method for evaluating the dopant contamination of the semiconductor wafer by a secondary ion mass spectroscopy (SIMS) or the like using chips being cut from the semiconductor wafer (for example, Japanese Unexamined Patent Publication (Kokai) No. 2004-207601).

SIMS is a method for impacting a surface of the cutout chip with primary ions, ionizing surface materials by sputter, and analyzing them with a mass spectrograph. According to this method, a distribution of the dopant concentration in a depth direction of the semiconductor wafer is first calculated, a difference between a value of the dopant concentration in the surface layer of the semiconductor wafer and a value of the dopant concentration in a bulk portion is then calculated from the concentration distribution, and the amount of dopant contamination in the surface layer portion of the semiconductor wafer is calculated from the difference.

This method is, however, a destructive evaluation in which the chips are cut out from the semiconductor wafer to be measured, and only the cutout chip portions can be measured, so that a map of the dopant in a plane has not been able to be obtained, in addition to spending a large amount of time and cost.

DISCLOSURE OF THE INVENTION

The present invention is made in view of such problems, and aims at providing a method for evaluating dopant contamination of a semiconductor wafer, which can calculate an amount of dopant contamination of a whole surface layer of the semiconductor wafer without contact, nondestructively, and accurately.

The present invention is made to solve the above-mentioned problems, and provides a method for evaluating dopant contamination of a semiconductor wafer, wherein a resistivity of a bulk portion of the semiconductor wafer is measured by an eddy current method, a resistivity in a surface layer of the semiconductor wafer is measured by a surface photovoltage method, and an amount of dopant contamination of the semiconductor wafer is calculated from a difference between a value of the resistivity of the bulk portion measured by the eddy current method and a value of the resistivity in the surface layer measured by the surface photovoltage method.

In the present invention, the resistivity of the bulk portion of the semiconductor wafer is measured by the eddy current method. According to this eddy current method, even when the surface layer is contaminated with dopant, it is possible to accurately measure the resistivity of the bulk portion, without hardly influenced. Meanwhile, in the present invention, the resistivity in the surface layer of the semiconductor wafer is measured by the surface photovoltage method, and this can also measure the resistivity in the surface layer accurately. Hence, it is possible to calculate the exact amount of dopant contamination from the difference between the value of the resistivity in the bulk portion measured by the eddy current method and the value of the resistivity in the surface layer measured by the surface photovoltage method.

In addition, according to the eddy current method and the surface photovoltage method, it is possible to quickly measure a wide area in a plane of the semiconductor wafer without contact and nondestructively. For this reason, the amount of dopant contamination of the whole surface layer of the semiconductor wafer can be calculated readily and accurately, and without contact and nondestructively.

In this case, it is possible that the measurements by the eddy current method and the surface photovoltage method are performed on the semiconductor wafer after heat treatment.

The surface layer of the semiconductor wafer after heat treatment may be contaminated with dopant from an atmosphere within a heat treat furnace, the heat treat furnace, or the like. In the present invention, however, since the resistivity of the bulk portion of the semiconductor wafer is measured by the eddy current method as mentioned above, the resistivity of the bulk portion of the wafer can be measured accurately irrespective of whether or not the surface layer of the wafer is contaminated by the dopant. For that reason, according to the present invention, even when it is the semiconductor wafer after heat treatment, the amount of dopant contamination can be calculated accurately.

As a matter of course, it is also possible that the measurement by the eddy current method is performed on the semiconductor wafer before heat treatment, and the measurement by the surface photovoltage method is performed on the semiconductor wafer after heat treatment.

However, since there is a case of the heat treatment in which the resistivity of the bulk portion of the wafer itself changes (donor killer heat treatments as an example), it is preferable in that case to perform both of the measurement by the eddy current method and the measurement by the surface photovoltage method on the semiconductor wafer after heat treatment in order to calculate the amount of dopant contamination accurately.

Moreover, in the method for evaluating dopant contamination of a semiconductor wafer of the present invention, it is possible that the dopant for which the contamination is evaluated includes at least one of P, B, Al, Ga, In, Sb, and As.

According to the present invention, the amount of contamination due to these dopants, which are generally used for the semiconductor wafer, and greatly affect resistivity characteristics thereof can be measured accurately.

Further, in the method for evaluating dopant contamination of a semiconductor wafer of the present invention, it is possible that the semiconductor wafer for which the dopant contamination is evaluated is a silicon wafer.

As for the silicon wafer, since a carrier concentration may be changed only by a small amount of a dopant mixing therein and the resistivity may be significantly changed, it is particularly important to accurately evaluate and manage the dopant contamination thereof. The present invention is a method particularly suitable for evaluating the dopant contamination of such a silicon wafer.

Further, in the method for evaluating dopant contamination of a semiconductor wafer of the present invention, it is possible that a map for indicating a dopant contamination distribution in the semiconductor wafer surface layer is created from the calculated amount of dopant contamination of the semiconductor wafer.

As described above, according to the surface photovoltage method, it is possible to measure the resistivity in a wide area in a plane of the wafer. Hence, measuring the resistivity in the surface layer over whole plane of the wafer by the method for the present invention makes it possible to create the map for indicating the dopant contamination distribution in the whole semiconductor wafer surface layer using the measurement results. As is understood, when the map for indicating the contamination distribution created as described above is used, the dopant contamination can be readily evaluated on the whole semiconductor wafer surface layer.

As described above, according to the present invention, the resistivity in the bulk portion of the semiconductor wafer is measured by the eddy current method, the resistivity in the surface layer of the semiconductor wafer is measured by the surface photovoltage method, and the amount of dopant contamination of the semiconductor wafer is calculated from the difference between the value of the resistivity of the bulk portion measured by the eddy current method and the value of the resistivity in the surface layer measured by the surface photovoltage method. As a result of this, it is possible to calculate the amount of dopant contamination of the whole surface layer of the semiconductor wafer without contact and nondestructively, and correctly and quickly.

BEST MODES FOR CARRYING OUT THE INVENTION

Hereinafter, the present invention will be described in detail, but the present invention is not limited thereto.

In the present invention, a resistivity of a semiconductor wafer surface layer is measured by a surface photovoltage method. When this method is used, a resistivity distribution of the semiconductor wafer surface layer can be measured quickly without contact and nondestructively. However, this method can measure only the resistivity in the surface layer. Hence, in order for a surface photovoltage method to evaluate dopant contamination of the semiconductor wafer, the only way is, for example, to consider that a resistivity at a wafer center is a resistivity of the wafer as a substrate in the obtained resistivity radial distribution of the wafer, and to perform a relative evaluation such that the dopant contamination is evaluated from a difference between these resistivities, or the like. If it is desired to evaluate an exact amount of contamination, it is necessary to cut the wafer into chips as described above and calculate for the resistivity distribution in a depth direction by an evaluation using a SIMS or a Spreading Resistance (SR) method. Such a method is destructive inspection, and chip cutting or the like is required for it, and it also requires time and cost.

Meanwhile, it is found out that measuring a resistivity of a bulk portion of the semiconductor wafer by an eddy current method makes it possible to accurately measure the resistivity of the bulk portion even if there is the dopant contamination in the surface layer in the present invention, and the present invention is accomplished by reaching an idea that the dopant contamination of the semiconductor wafer can be measured simply and accurately, and without contact and nondestructively by combining this eddy current method with the aforementioned surface photovoltage method.

Figure 1:
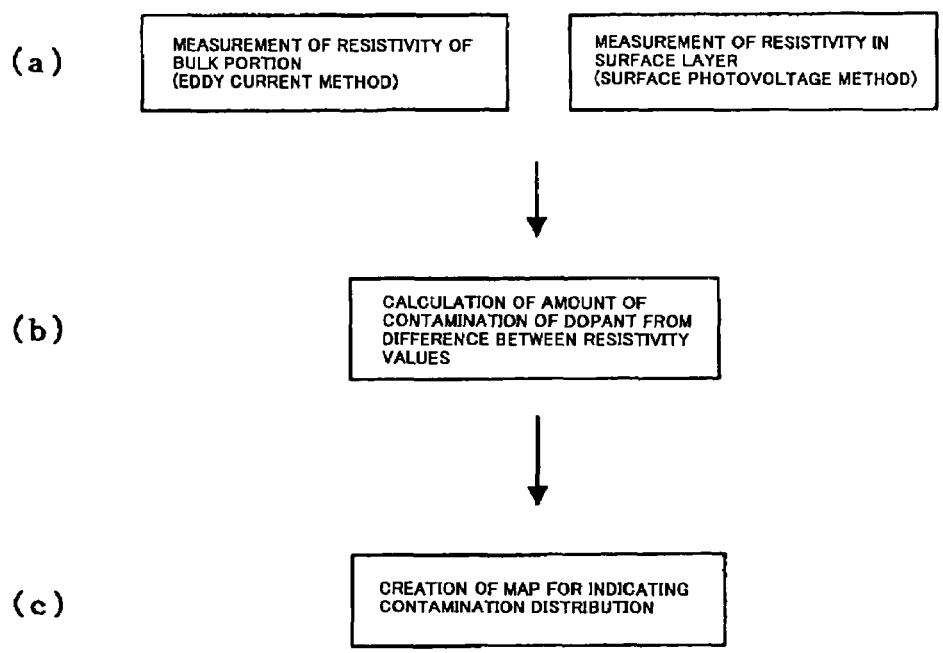
FIG. 1 is a flow chart illustrating an example of a method for evaluating dopant contamination in accordance with the present invention.

FIG. 1 is a flow chart illustrating an example of a method for evaluating dopant contamination of a semiconductor wafer in accordance with the present invention.

First, a resistivity of a bulk portion of the semiconductor wafer is measured by the eddy current method, and a resistivity in a surface layer of the semiconductor wafer is measured by the surface photovoltage method as shown in FIG. 1(a).

Next, an amount of dopant contamination of the semiconductor wafer is calculated from a difference between a value of the resistivity in the bulk portion measured by the eddy current method and a value of the resistivity in the surface layer measured by the surface photovoltage method as shown in FIG. 1(b).

The resistivity of the bulk portion is the original resistivity of the semiconductor wafer and shows the resistivity of the semiconductor wafer before contamination, and the resistivity in the surface layer shows a resistivity different from that of the bulk portion, once it is contaminated by heat treatment or the like. For that reason, the amount of dopant contamination can be calculated from the difference between the values of these measured resistivities.

Figure 3:
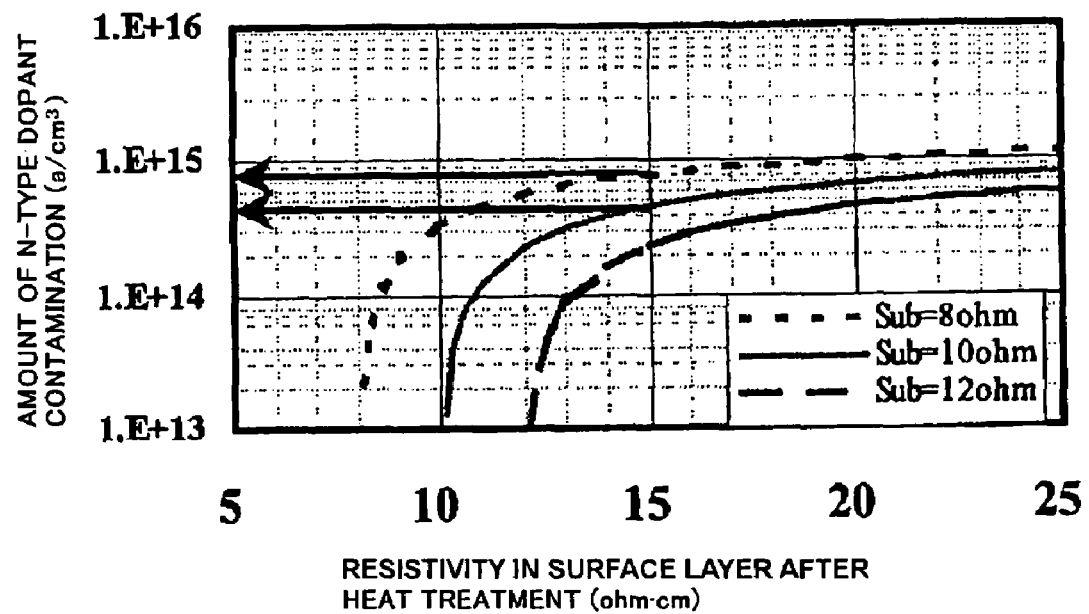
FIG. 3 is a graph for indicating a relation between a resistivity in a surface layer of a silicon wafer after heat treatment, and an amount of contamination due to n-type dopant.

For example, referring to FIG. 3 for a description, when a p-type silicon wafer whose resistivity before contamination (resistivity of the bulk portion) is 8 Ω·cm is subjected to heat treatment and the resistivity in the surface layer of the silicon wafer subjected to the heat treatment is measured, if the resistivity in the surface layer after the heat treatment (resistivity after contamination) is increased to 15 Ω·cm, it is contaminated with n-type dopant, and the amount of dopant contamination is 8e14 atoms/cm$^3$ ($8 \times 10^{14}$ atoms/cm$^3$).

Meanwhile, as can be seen from FIG. 3, for example, when the silicon wafer whose resistivity before contamination is actually 8 Ω·cm is erroneously measured as 10 Ω·cm, if the resistivity in the surface layer after the heat treatment (resistivity after contamination) is 15 Ω·cm, the amount of n-type dopant contamination calculated by the above-mentioned calculation method will results in 4e14 atoms/cm$^3$ which should be 8e14 atoms/cm$^3$, leading to estimation lower than the actual amount. This error is high when managing the amount of dopant contamination to a low concentration level, for example not more than 1e14 atoms/cm$^3$. In addition, as for the silicon wafer to be delivered, the resistivity varies within a standard such that the standard is, for example, 8 to 12 Ω·cm, as described above. For that reason, calculation accuracy of the amount of dopant contamination may deteriorate further.

Figure 4:
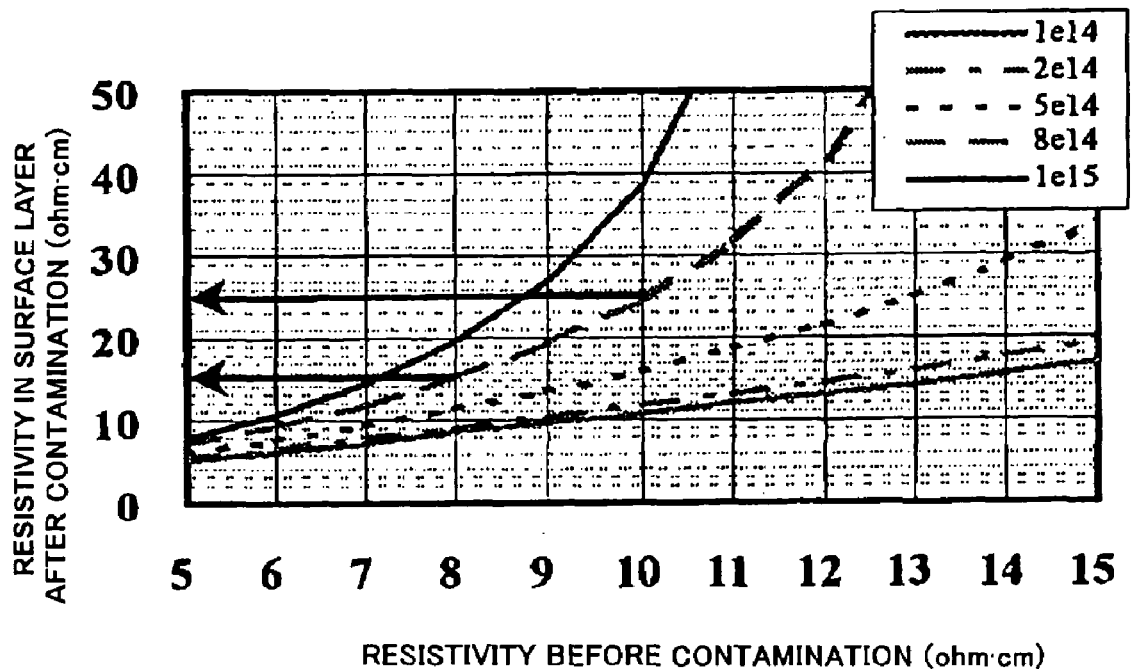
FIG. 4 is a graph for indicating a relation between a resistivity before contamination of the silicon wafer, and a resistivity in the surface layer after contamination.

Moreover, in other words, even for a semiconductor wafer contaminated by the dopant by the same amount, a resistivity of a contaminated portion thereof will significantly change depending on a resistivity before contamination (refer to FIG. 4).

In FIG. 4, a horizontal axis represents the resistivity of the semiconductor wafer before contamination, and a vertical axis represents the resistivity in the surface layer after contamination. For example, even when the amount of contamination due to n-type dopant is the same of 8e14 atoms/cm$^3$, the resistivity in the surface layer of the contaminated portion in a case where the resistivity before contamination is 8 Ω·cm is greatly different from that in a case where it is 10 Ω·cm.

Note herein that, FIG. 3 and FIG. 4 are created utilizing Irvine's equation (refer to ASTM F723).

As a result, in order to calculate the amount of dopant contamination accurately, a measured value of the resistivity of the semiconductor wafer before contamination (resistivity of the bulk portion) needs to be accurate in particular. Hence, just measuring the resistivity distribution in the surface layer by the aforementioned surface photovoltage method can not allow the dopant contamination to be accurately evaluated.

For that reason, the eddy current method is used for the measurement of the resistivity of the bulk portion in the present invention. It turned out that this eddy current method is the method for accurately measuring the resistivity of the bulk portion of the semiconductor wafer without contact and nondestructively, even when the surface layer is contaminated with dopant.

The eddy current method is the method for measuring the resistivity by the eddy current without contact, and a relation between a sheet conductivity σw of the semiconductor wafer and an eddy current detecting voltage Vσ when using an air core coil is given with a following equation in the method for detecting with an excitation coil.

$$V\sigma = \sigma w f^2 n_1 n_2 I_0 a k\sigma$$

Where, f is an excitation frequency, $n_1 n_2$ is the number of turns of the coil, $I_o$ is a current flowing through the excitation coil, kσ is a coefficient, and a is a radius of the coil.

Figure 2:
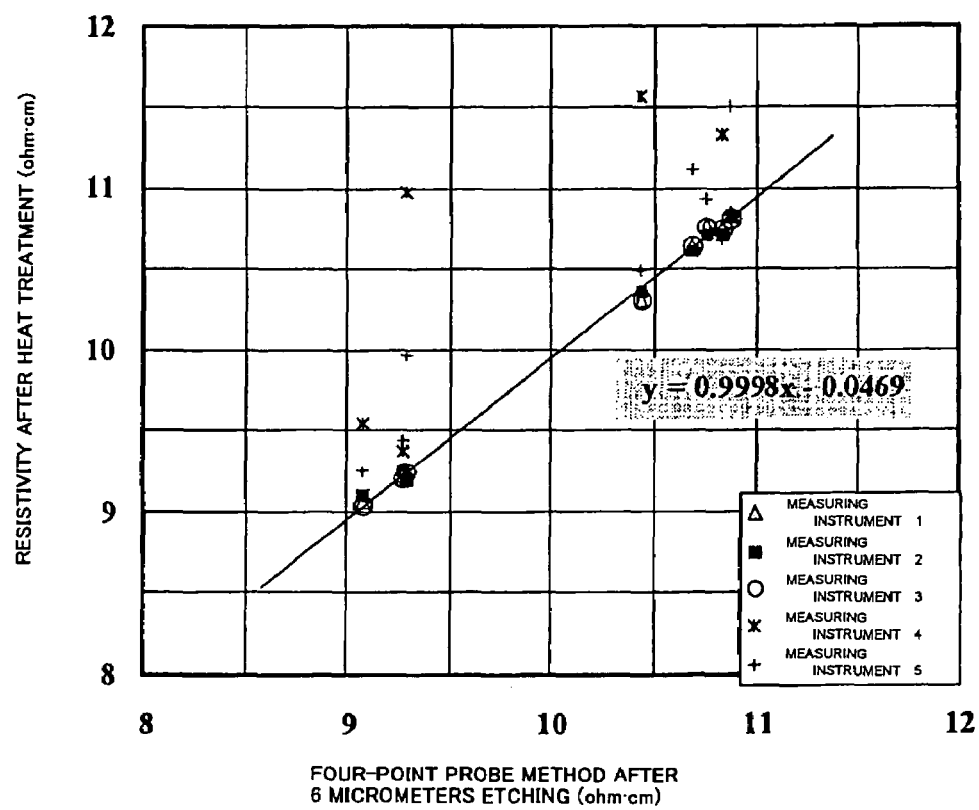
FIG. 2 is a graph for comparing results obtained by measuring a resistivity of a silicon wafer after heat treatment by an eddy current method and other methods.

Now, FIG. 2 is a graph for comparing results of measuring the resistivity of the silicon wafer after heat treatment by the eddy current method (measuring instrument 1: made by Kobelco company, measuring instrument 3: made by ADE company), and other methods (measuring instrument 4: CV method, measuring instrument 5: SR method).

The measurement here is performed according to the following order. First, the resistivity of the silicon wafer is measured in advance with a four-point probe method (measuring instrument 2: made by Napson company). Next, this silicon wafer is subjected to heat treatment. During this heat treatment, the surface layer of the silicon wafer is contaminated with dopant. Next, the resistivity of the wafer subjected to the heat treatment is measured by the eddy current method (measuring instruments 1 and 3) and other methods (measuring instruments 4 and 5). Next, the surface layer of the silicon wafer is removed by 6 μm by etching. Finally, the resistivity of the silicon wafer whose surface layer has been removed is again measured by the four-point probe method. The result of measuring by the four-point probe method after this surface layer etching is a true resistivity of the bulk portion of the silicon wafer after the heat treatment. This value is completely matched with the resistivity in the wafer surface measured before the heat treatment by the four-point probe method.

In FIG. 2, a vertical axis represents the resistivity measured by the eddy current method and other methods after the silicon wafer is heat-treated, and a horizontal axis represents the resistivity subsequently measured by the four-point probe method when the silicon wafer from which the surface layer has been removed. Namely, it means that the more the resistivity by the eddy current method or the like is close to the resistivity when measuring by the four-point probe method after the surface layer removal, the more the resistivity of the bulk portion can be accurately measured by the measuring method. In addition, the resistivity of the bulk portion will be coincident with the original wafer resistivity as mentioned above.

As can be seen from FIG. 2, according to the eddy current method (measuring instruments 1 and 3) although the surface layer is contaminated with dopant, it is accurately coincident with the resistivity of the bulk portion, allowing highly accurate measurement. Hence, the resistivity of the bulk portion can be measured for the semiconductor wafer after heat treatment by the eddy current method.

Meanwhile, in order to accurately calculate the amount of dopant contamination, naturally, it is necessary to also measure accurately the resistivity in the surface layer of the semiconductor wafer after heat treatment (after contamination). For that reason, the surface photovoltage method is used for the measurement of the resistivity in the surface layer in the present invention. This surface photovoltage method is the method for accurately measuring the resistivity in the surface layer of the semiconductor wafer and its distribution without contact and nondestructively.

The measurement principle of the surface photovoltage method is as follows. When a light with energy (hv) not less than the bandgap energy of Si is irradiated on a sample surface of the wafer in a thermal equilibrium state, excess carriers will be generated in the penetration depth corresponding to a wavelength of the irradiated light. Generated electrons and holes move to a surface side and an edge of a depletion layer, respectively. A generated minority carrier (electron e in a p-type semiconductor) change a surface barrier height by $\delta VS$. This potential $\delta VS$ is called an SPV value. It is possible to calculate a depletion layer width Wd using this SPV value according to the next equation (1).

$$\delta VS = -j(\delta\phi/\omega)(1-R)q(Wd/\in S) \quad (1)$$

Where, j is an imaginary unit, $\phi$ is excitation light intensity, $\omega$ is an angular frequency of the excitation light, R is a reflectance of the wafer surface, q is a unit charge amount, and $\in S$ is a dielectric constant of the semiconductor. The depletion layer width Wd calculated by the surface photovoltage method is assumed to be the maximum depletion layer width Wmax, and a carrier concentration NS can be calculated from the next equation (2).

$$W\max = [2 \in SkT \ln(NS/ni)/q^2NS]^{1/2} \quad (2)$$

Where, k represents the Boltzmann constant, T represents the absolute temperature, and ni represents an intrinsic free carrier concentration.

When an excitation light source with a short wavelength, for example 450 nm, which is shorter than that is used for the normal surface photovoltage method as the excitation light source used for the measurement at this time, the penetration depth of the light will be not more than 0.4 μm, so that it is possible to calculate for the carrier concentration (strictly dopant concentration) of only the wafer surface layer.

Once the carrier concentration is calculated like this, a conversion from the carrier concentration to the resistivity can be performed using the Irvine's equation (refer to ASTM F723).

Note herein that, although the surface photovoltage method is a method by which it is possible to measure the resistivity in a surface layer of a semiconductor wafer accurately as described above, an amount of dopant contamination cannot be accurately measured even when a calculation is tried only from the resistivity measured by the surface photovoltage method as described above.

The reason is that, since the surface photovoltage method can calculate only the resistivity in the surface layer of the semiconductor wafer, when the amount of dopant contamination is calculated only by the surface photovoltage method, the resistivity in the surface layer at, for example, the wafer center is considered as the resistivity of the bulk portion, and the amount of dopant contamination will be calculated from a difference between this and the resistivity of a contaminated portion of the surface layer. Hence, it is premised that the surface layer at the wafer center is not contaminated with dopant.

As a result, this method may cause a problem of calculating for an incorrect amount of dopant contamination when the surface layer at the wafer center is contaminated with dopant.

Figure 5:
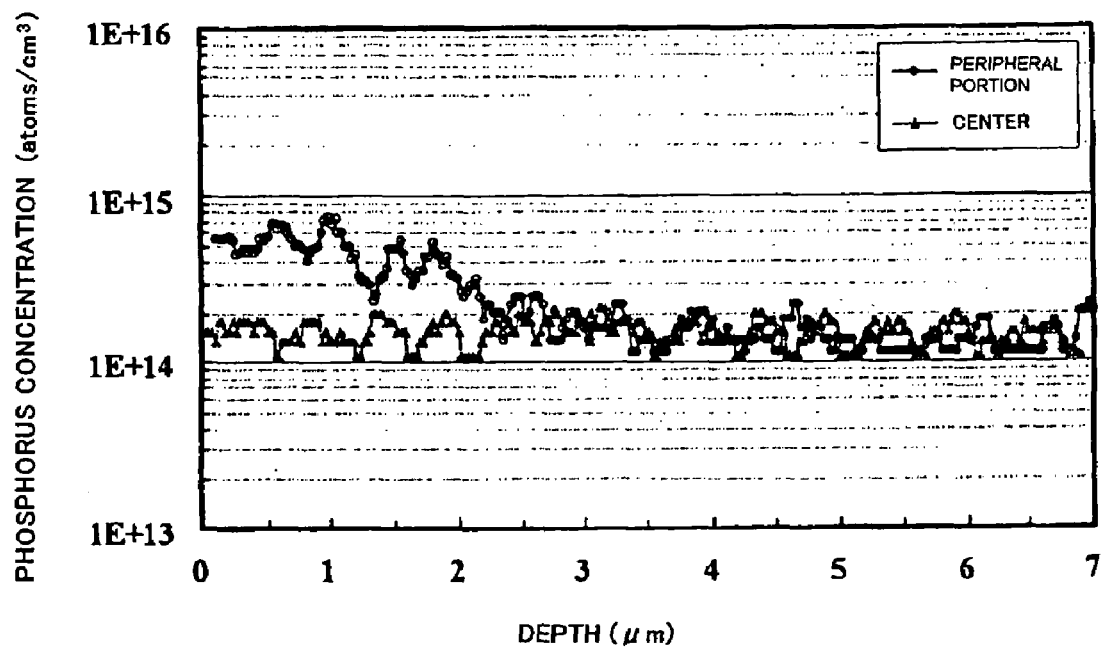
FIG. 5 is a graph for indicating a phosphorus concentration distribution of the silicon wafer (samples 1 and 2), here (a) represents sample 1 and (b) represents sample 2.
Figure 5:
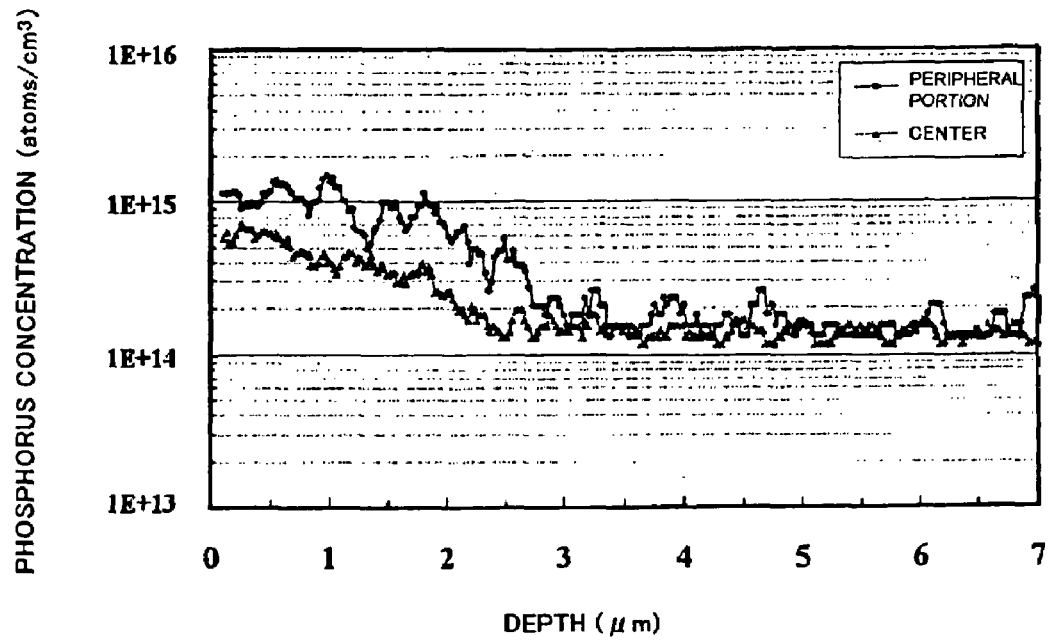
Figure 8:
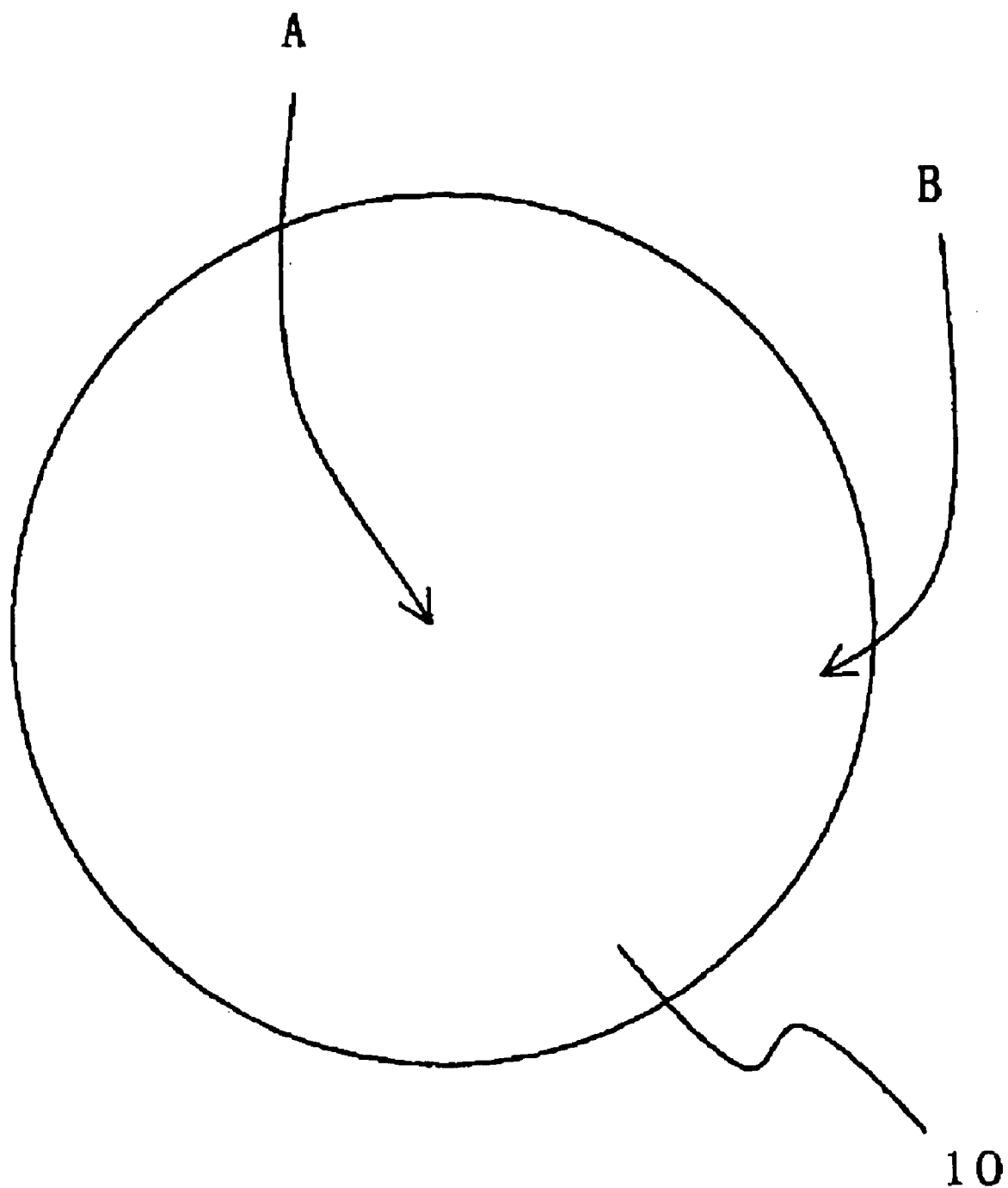
FIG. 8 is a pattern diagram for indicating measurement points of the phosphorus concentration distribution shown in FIG. 5.

When an example is shown, FIG. 5 is a graph showing a phosphorus concentration distribution of the silicon wafer after heat treatment. The phosphorus concentration from the surface to a depth of 7 μm is measured by SIMS for two samples (FIG. 5(a): sample 1, FIG. 5(b): sample 2), and it is then created using measurement results. Measurement points are at a center A and an outer peripheral portion B of a wafer 10, as shown in FIG. 8.

Figure 6:
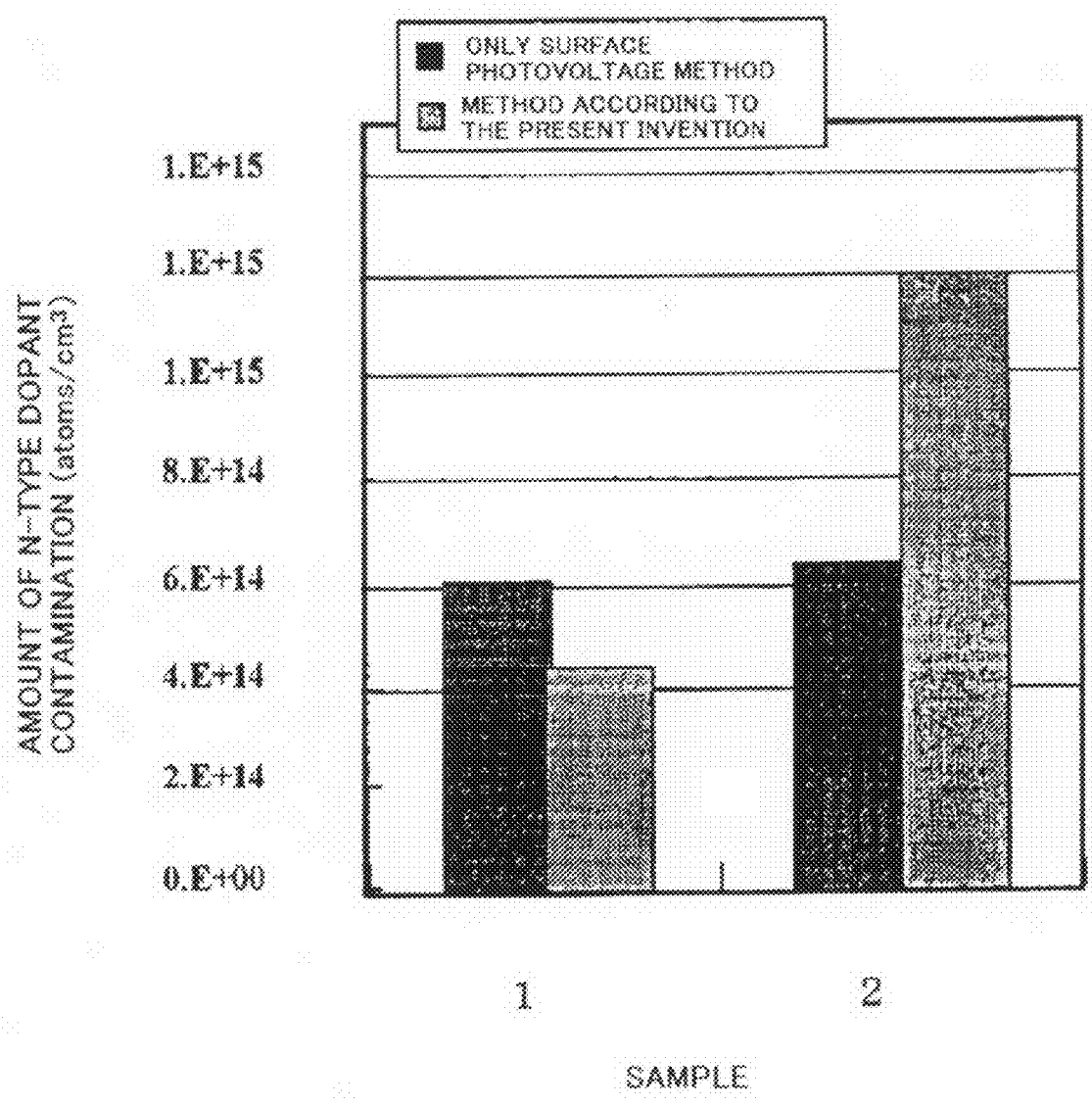
FIG. 6 is a graph for comparing a case where an amount of n-type dopant contamination of respective samples (samples 1 and 2) in FIG. 5 is calculated only by a surface photovoltage method with a case where it is calculated by the method according to the present invention.

Meanwhile, FIG. 6 is a graph comparing amounts of phosphorus contamination of respective samples (samples 1 and 2) in FIG. 5 with each other, one is calculated only by the surface photovoltage method (the amount of contamination is provided by the difference between the resistivity in the surface layer at the wafer center, and the resistivity in the surface layer of the contaminated portion), and the other is calculated by the method according to the present invention (the each resistivity of the bulk portion of samples 1 and 2 is calculated by the eddy current method, and the amount of contamination is provided by the difference between this and the value due to the surface photovoltage method). The left-hand side of each bar graph is based only on the surface photovoltage method, and the right-hand side thereof is the method according to the present invention.

In FIG. 5, in the sample 1, the phosphorus concentration of the surface layer at the wafer center is about $1.1 \times 10^{14}$ atoms/cm$^3$, and is hardly contaminated with dopant, whereas the phosphorus concentration of the surface layer of the outer peripheral portion of the wafer is about $7 \times 10^{14}$ atoms/cm$^3$. Meanwhile, in the sample 2, the phosphorus concentration of the surface layer at the wafer center is about $7 \times 10^{14}$ atoms/cm$^3$, and is contaminated with dopant, whereas the phosphorus concentration of the surface layer of the outer peripheral portion of the wafer is about $1.1 \times 10^{15}$ atoms/cm$^3$, and it is also heavily contaminated therewith.

In spite of that, the sample 1 and the sample 2 result in having almost the same amount of dopant contamination when it is calculated only by the surface photovoltage method, as can be seen from FIG. 6. The reason is that the differences between the resistivity in the surface layer at the wafer center and the resistivity in the surface layer of the contaminated portion are almost the same in the sample 1 and the sample 2. As is understood, when the surface layer at the semiconductor wafer center is contaminated, the amount of dopant contamination cannot be accurately measured only by the surface photovoltage method. Meanwhile, according to the method of the present invention, the amount of dopant contamination can be accurately calculated as can be seen from FIG. 5 and FIG. 6.

Additionally, according to the eddy current method or the surface photovoltage method, it is possible to measure a wide area in a plane without contact and nondestructively. Since the measurement can be performed without contact and nondestructively as described above, the semiconductor wafer after the measurement can be used as a product as it is, and alternatively it can also be used for another examination.

Moreover, according to the eddy current method, the resistivity of the bulk portion can be accurately measured even for the semiconductor wafer whose surface layer is contaminated, as described above. Hence, the measurement by the eddy current method can also be performed on the semiconductor wafer after heat treatment with the measurement by the surface photovoltage method. At this time, the measurement by the eddy current method may be performed first, and the measurement by the surface photovoltage method may be subsequently performed, and on the contrary, the measurement by the surface photovoltage method may be performed first, and the measurement by the eddy current method may be subsequently performed.

As described above, when the measurements by the eddy current method and the surface photovoltage method are successively performed on the semiconductor wafer after heat treatment, it is not necessary to refer the consistency between the data measured by the eddy current method and the data measured by the surface photovoltage method, resulting in easy accumulation of the measurement results.

As a matter of course, the measurement by the eddy current method may be performed on the semiconductor wafer before heat treatment, and the measurement by the surface photovoltage method may be performed on the semiconductor wafer after heat treatment.

According to the present invention, a map for indicating the dopant contamination distribution in the semiconductor wafer surface layer can be further created from the calculated amount of dopant contamination of the semiconductor wafer as shown in FIG. 1(c). The reason is that since the resistivity distribution in the surface layer can be accurately measured in a wide area in a plane according to the surface photovoltage method as described above, the distribution of the difference between it and the resistivity of the bulk portion by the eddy current method can be easily calculated when this data is used.

Figure 7:
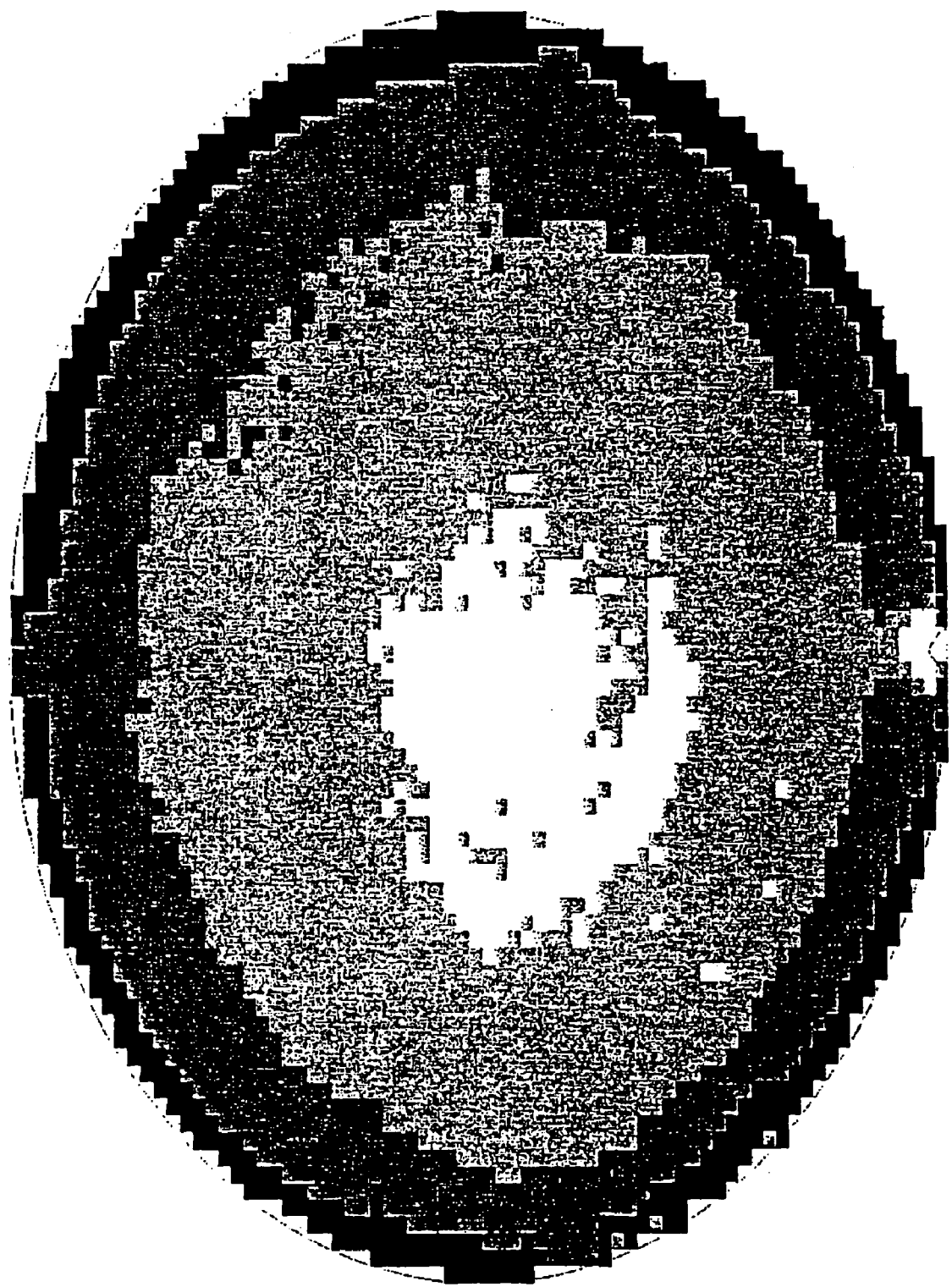
FIG. 7 is a map for indicating a dopant contamination distribution.

A map showing the dopant contamination distribution created like this is FIG. 7. As the amount of contamination becomes larger, it is indicated with deeper color. It is understood from FIG. 7 that the amount of dopant contamination is not uniform on the whole wafer, and the amount of contamination of the peripheral portion of the wafer is high as compared with the center thereof. As described above, the evaluation of the dopant contamination of the semiconductor wafer becomes easy by visualizing the contamination distribution.

Incidentally, the present invention is not limited to the above embodiments. The aforementioned embodiments are only exemplifications, and what has substantially the same configuration and exerts substantially the same effect as what is described in the claims of the invention belongs to the technical scope of the invention.

Although the phosphorus contamination of the silicon wafer has mainly been described, for example, in the above description, the present invention can also be adapted to a case of evaluating the contamination with dopant, such as B, Al, Ga, In, P, Sb, and As, which are usually used for the semiconductor wafers as far as a resistivity changes with contamination due to them. Moreover, the semiconductor wafer used for the evaluation may be a wafer of compound semiconductors, such as GaAs.

The invention claimed is:

1. A method for evaluating dopant contamination of a semiconductor wafer, wherein
a resistivity of a bulk portion of the semiconductor wafer is measured by an eddy current method,
a resistivity in a surface layer of the semiconductor wafer is measured by a surface photovoltage method, and
an amount of dopant contamination of the semiconductor wafer is calculated from a difference between a value of the resistivity of the bulk portion measured by the eddy current method and a value of the resistivity in the surface layer measured by the surface photovoltage method.

2. The method for evaluating dopant contamination of a semiconductor wafer according to claim 1, wherein the measurements by the eddy current method and the surface photovoltage method are performed on the semiconductor wafer after heat treatment.

3. The method for evaluating dopant contamination of a semiconductor wafer according to claim 2, wherein the dopant for which the contamination is evaluated includes at least one of P, B, Al, Ga, In, Sb, and As.0.

4. The method for evaluating dopant contamination of a semiconductor wafer according to claim 3, wherein the semiconductor wafer for which the dopant contamination is evaluated is a silicon wafer.

5. The method for evaluating dopant contamination of a semiconductor wafer according to claim 4, wherein a map for indicating a dopant contamination distribution in the semiconductor wafer surface layer is created from the calculated amount of dopant contamination of the semiconductor wafer.

6. The method for evaluating dopant contamination of a semiconductor wafer according to claim 3, wherein a map for indicating a dopant contamination distribution in the semiconductor wafer surface layer is created from the calculated amount of dopant contamination of the semiconductor wafer.

7. The method for evaluating dopant contamination of a semiconductor wafer according to claim 2, wherein the semiconductor wafer for which the dopant contamination is evaluated is a silicon wafer.

8. The method for evaluating dopant contamination of a semiconductor wafer according to claim 7, wherein a map for indicating a dopant contamination distribution in the semiconductor wafer surface layer is created from the calculated amount of dopant contamination of the semiconductor wafer.

9. The method for evaluating dopant contamination of a semiconductor wafer according to claim 2, wherein a map for indicating a dopant contamination distribution in the semiconductor wafer surface layer is created from the calculated amount of dopant contamination of the semiconductor wafer.

10. The method for evaluating dopant contamination of a semiconductor wafer according to claim 1, wherein the measurement by the eddy current method is performed on the semiconductor wafer before heat treatment, and, the measurement by the surface photovoltage method is performed on the semiconductor wafer after heat treatment.

11. The method for evaluating dopant contamination of a semiconductor wafer according to claim 10, wherein the dopant for which the contamination is evaluated includes at least one of P, B, Al, Ga, In, Sb, and As.

12. The method for evaluating dopant contamination of a semiconductor wafer according to claim 11, wherein the semiconductor wafer for which the dopant contamination is evaluated is a silicon wafer.

13. The method for evaluating dopant contamination of a semiconductor wafer according to claim 12, wherein a map for indicating a dopant contamination distribution in the semiconductor wafer surface layer is created from the calculated amount of dopant contamination of the semiconductor wafer.

14. The method for evaluating dopant contamination of a semiconductor wafer according to claim 11, wherein a map for indicating a dopant contamination distribution in the semiconductor wafer surface layer is created from the calculated amount of dopant contamination of the semiconductor wafer.

15. The method for evaluating dopant contamination of a semiconductor wafer according to claim 10, wherein the semiconductor wafer for which the dopant contamination is evaluated is a silicon wafer.

16. The method for evaluating dopant contamination of a semiconductor wafer according to claim 15, wherein a map for indicating a dopant contamination distribution in the semiconductor wafer surface layer is created from the calculated amount of dopant contamination of the semiconductor wafer.

17. The method for evaluating dopant contamination of a semiconductor wafer according to claim 10, wherein a map for indicating a dopant contamination distribution in the semiconductor wafer surface layer is created from the calculated amount of dopant contamination of the semiconductor wafer.

18. The method for evaluating dopant contamination of a semiconductor wafer according to claim 1, wherein the dopant for which the contamination is evaluated includes at least one of P, B, Al, Ga, In, Sb, and As.

19. The method for evaluating dopant contamination of a semiconductor wafer according to claim 18, wherein the semiconductor wafer for which the dopant contamination is evaluated is a silicon wafer.

20. The method for evaluating dopant contamination of a semiconductor wafer according to claim 19, wherein a map for indicating a dopant contamination distribution in the semiconductor wafer surface layer is created from the calculated amount of dopant contamination of the semiconductor wafer.

21. The method for evaluating dopant contamination of a semiconductor wafer according to claim 18, wherein a map for indicating a dopant contamination distribution in the semiconductor wafer surface layer is created from the calculated amount of dopant contamination of the semiconductor wafer.

22. The method for evaluating dopant contamination of a semiconductor wafer according to claim 1, wherein the semiconductor wafer for which the dopant contamination is evaluated is a silicon wafer.

23. The method for evaluating dopant contamination of a semiconductor wafer according to claim 22, wherein a map for indicating a dopant contamination distribution in the semiconductor wafer surface layer is created from the calculated amount of dopant contamination of the semiconductor wafer.

24. The method for evaluating dopant contamination of a semiconductor wafer according to claim 1, wherein a map for indicating a dopant contamination distribution in the semiconductor wafer surface layer is created from the calculated amount of dopant contamination of the semiconductor wafer.

* * * * *